United States Patent [19]

Beckmann et al.

[11] Patent Number: 5,738,806
[45] Date of Patent: Apr. 14, 1998

[54] THIENOTHIENYLAZOANILINES IN NONLINEAR OPTICS

[75] Inventors: Stefan Beckmann, Mannheim; Karl-Heinz Etzbach, Frankenthal; Ruediger Sens, Mannheim, all of Germany

[73] Assignee: BASF Aktiengesellschaft, Ludwigshafen, Germany

[21] Appl. No.: 635,974

[22] PCT Filed: Nov. 9, 1994

[86] PCT No.: PCT/EP94/03685

§ 371 Date: May 8, 1996

§ 102(e) Date: May 8, 1996

[87] PCT Pub. No.: WO95/14957

PCT Pub. Date: Jun. 1, 1995

[30] Foreign Application Priority Data

Nov. 22, 1993 [DE] Germany ............ 43 39 712.3

[51] Int. Cl.$^6$ .......... F21V 9/00; C08F 228/06; C09B 29/033
[52] U.S. Cl. .......... 252/582; 354/752; 354/753; 526/256; 526/257; 526/312
[58] Field of Search .......... 252/299.01, 299.68, 252/582; 526/256, 257, 312; 354/752, 753

[56] References Cited

U.S. PATENT DOCUMENTS

| Re. 35,407 | 12/1996 | Wiesenfeldt et al. | 526/256 |
|---|---|---|---|
| 4,843,153 | 6/1989 | Eilingsfeld et al. | 534/752 |
| 5,264,507 | 11/1993 | Wiesenfeldt et al. | 526/256 |
| 5,434,231 | 7/1995 | Wiesenfeldt et al. | 526/256 |
| 5,461,131 | 10/1995 | Wiesenfeldt et al. | 526/256 |

OTHER PUBLICATIONS

Angew. Chem. 96 (1984) 637–651, Von David J. Williams.

J. Polymer Sci., Part A, Polymer Chem. vol. 28, (1990), 1–13, Douglas R. Robello.

Z. Naturforschung vol. 20a (1965), 1441–1471, W. Liptay.

J. Org. Chem., vol. 54, (1989), 3775–3778.

Chemistry and Industry, 1990, pp. 600 to 608.

*Primary Examiner*—Shean C. Wu
*Attorney, Agent, or Firm*—Oblon, Spivak, McClelland, Maier & Neustadt, P.C.

[57] ABSTRACT

Use of azo dyes having a diazo component derived from an aminothienothiophene and a coupling component of the aniline series in nonlinear optics, polymers derived from these azo dyes, the use thereof in nonlinear optics, and novel phenylthienothienylazoanilines.

10 Claims, No Drawings

THIENOTHIENYLAZOANILINES IN NONLINEAR OPTICS

This application is a 371 of PCT/EP44/03685 filed on Nov. 9, 1994.

DESCRIPTION

The present invention relates to the use in nonlinear optics of azo dyes having a diazo component derived from an aminothienothiophene and a coupling component of the aniline series, to polymers derived from these azo dyes, to the use thereof in nonlinear optics, and to novel phenylthienothienylazoanilines.

The nonlinear optical properties of organic compounds find application in many areas of optoelectronics. Examples are applications in frequency doubling, phase modulators, optical amplifiers, interferometers, optical switches or communications technology.

It is common knowledge that organic materials, in particular polymers with certain chromophores, can have nonlinear optical properties which are in some instances more considerable than those of comparable inorganic materials. The materials currently used most frequently are inorganic crystals, for example of potassium dihydrogenphosphate or lithium niobate. These crystals are complicated and costly to produce and, owing to their rigid structure, difficult to use in optical equipment. A further disadvantage is the smallness of their nonlinear effects.

A particular advantage of suitable organic chromophores and their use in polymeric materials is their simple preparation and processing.

The chromophores used in nonlinear optics are generally used either in crystalline form or in polymer-bound form.

Angew. Chem. 96 (1984), 637–651, discloses the use of stilbene derivatives or specific azo dyes for this purpose.

It is an object of the present invention to provide suitable thienothienylazo dyes which are advantageous for use in polymeric nonlinear optical systems. More particularly, such azo compounds shall have large hyperpolarizability values, good thermal stability, good compatibility with the polymers used in nonlinear optical systems, and good film-forming properties with copolymers.

We have found that this object is achieved by azo dyes of the formula I

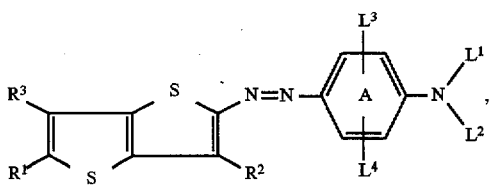   (I)

where
the ring A may be benzofused,
$L^1$ and $L^2$ are each independently of the other hydrogen, unsubstituted or phenyl-, hydroxyl-, acryloyloxy- or methacryloyloxy-substituted $C_1$-$C_{10}$-alkyl, or phenyl, or $L^1$ and $L^2$ are together with the nitrogen atom joining them together pyrrolidinyl, piperidinyl, morpholinyl, piperazinyl or N-($C_1$-$C_4$-alkyl)piperazinyl,
$L^3$ and $L^4$ are each independently of the other hydrogen, $C_1$-$C_{10}$-alkyl, $C_5$-$C_7$-cycloalkyl, $C_1$-$C_{10}$-alkoxy, cyano or halogen,
$R^1$ is hydrogen, halogen, nitro, hydroxysulfonyl, formyl, cyano, carbamoyl, dicyanovinyl or a radical of the formula $COX^1$, $COOX^1$, $CONX^1X^2$, $CH=N-X^3$, $CH=C(NO_2)-X^4$ or

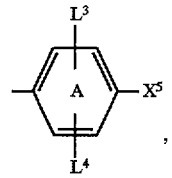, where $X^1$ and $X^2$ are each independently of the other $C_1$-$C_{10}$-alkyl, which may be phenyl-substituted, $C_5$-$C_7$-cycloalkyl or phenyl, $X^3$ is hydroxyl or phenylamino, $X^4$ is hydrogen or $C_1$-$C_4$-alkyl, and $X^5$ is hydrogen, nitro, hydroxysulfonyl, formyl, cyano, $C_1$-$C_4$-alkylsulfonyl, dicyanovinyl or a radical of the formula $COX^1$, $COOX^1$, $CONX^1X^2$, $CH=N-X^3$ or $CH=C(NO_2)-X^4$, where $X^1$, $X^2$, $X^3$ and $X^4$ are each as defined above, and the ring A and $L^3$ and $L^4$ are each as defined above,
$R^2$ is hydrogen, nitro, cyano, carboxyl or a radical of the formula $COX^1$, $COOX^1$ or $CONX^1X^2$, where $X^1$ and $X^2$ are each as defined above, and
$R^3$ is hydrogen, $C_1$-$C_{10}$-alkyl, which may be phenyl-substituted, $C_5$-$C_7$-cycloalkyl, phenyl or $C_1$-$C_{10}$-alkoxy, in that they are advantageous for use in nonlinear optics.

Any alkyl appearing in the abovementioned formula I may be straight-chain or branched.

In substituted alkyl appearing in the abovementioned formula I the number of substituents is generally 1 or 2.

$L^1$, $L^2$, $L^3$, $L^4$, $X^1$, $X^2$, $X^4$ and $R^3$ are each for example methyl, ethyl, propyl, isopropyl, butyl, isobutyl or sec-butyl.

$L^1$, $L^2$, $L^3$, $L^4$, $X^1$, $X^2$ and $R^3$ may each also be for example pentyl, isopentyl, neopentyl, tert-pentyl, hexyl, 2-methylpentyl, heptyl, octyl, 2-ethylhexyl, isooctyl, nonyl, isononyl, decyl or isodecyl (the above designations isooctyl, isononyl and isodecyl are trivial names derived from the oxo process alcohols—cf. Ullmanns Encyklopädie der technischen Chemie, 4th edition, volume 7, pages 215 to 217, and volume 11, pages 435 and 436).

$L^3$, $L^4$ and $R^3$ may each also be for example cyclopentyl, cyclohexyl, cycloheptyl, methoxy, ethoxy, propoxy, isopropoxy, butoxy, isobutoxy, sec-butoxy, pentyloxy, isopentyloxy, neopentyloxy, tert-pentyloxy, hexyloxy, 2-methylpentyloxy, heptyloxy, octyloxy, 2-ethylhexylexy, isooctyloxy, nonyloxy, isononyloxy, decyloxy or isodecyloxy.

$L^1$, $L^2$ and $R^3$ may each also be for example benzyl or 1- or 2-phenylethyl.

$L^1$ and $L^2$ may each also be for example 2-hydroxyethyl, 2- or 3-hydroxypropyl, 2- or 4-hydroxybutyl, 5-hydroxypentyl, 6-hydroxyhexyl, 7-hydroxyheptyl, 8-hydroxyoctyl, 9-hydroxynonyl, 10-hydroxydecyl, 2-acryloyloxyethyl, 2-methacryloyloxyethyl, 2- or 3-acryloyloxypropyl, 2- or 3-methacryloyloxypropyl, 2- or 4-acryloyloxybutyl, 2- or 4-methacryloyloxybutyl, 5-acryloyloxypentyl, 5-methacryloyloxypentyl, 6-acryloyloxyhexyl, 6-methacryloyloxyhexyl, 7-acryloyloxyheptyl, 7-methacryloyloxyheptyl, 8-acryloyloxyoctyl, 8-methacryloyloxyoctyl, 9-acryloyloxynonyl, 9-methacryloyloxynonyl, 10-acryloyloxydecyl or 10-methacryloyloxydecyl.

$L^3$ and $L^4$ may each also be for example fluorine, chlorine, bromine or iodine.

$X^5$ is for example methylsulfonyl, ethylsulfonyl, propylsulfonyl, isopropylsulfonyl, butylsulfonyl, isobutylsulfonyl or sec-butylsulfonyl.

Preference is given to the use according to the invention of azo dyes of the formula I where $L^1$ and $L^2$ are each independently of the other $C_1$-$C_4$-alkyl, $C_2$-$C_8$-hydroxyalkyl, $C_2$-$C_8$-acryloyloxyalkyl or $C_2$-$C_8$-methacryloyloxyalkyl, or $L^1$ and $L^2$ are together with the nitrogen atom joining them together pyrrolidinyl or piperidinyl.

Preference is further given to the use according to the invention of azo dyes of the formula I where $L^3$ and $L^4$ are each hydrogen.

Preference is further given to the use according to the invention of azo dyes of the formula I where the ring A is nonbenzofused.

Preference is further given to the use according to the invention of azo dyes of the formula I where $R^1$ is $C_1$-$C_6$-alkoxycarbonyl, formyl, acetyl, dicyanovinyl or a radical of the formula

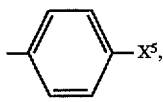

wherein $X^5$ is as defined above, especially hydrogen, nitro, formyl, cyano, methylsulfonyl or dicyanovinyl, $R^2$ is cyano and $R^3$ is hydrogen.

Dicyanovinyl is in particular 2,2-dicyanovinyl.

The azo dyes of the formula I are partly known and described for example in U.S. Pat. No. 4,843,153.

The present invention further provides azo dyes of the formula Ia

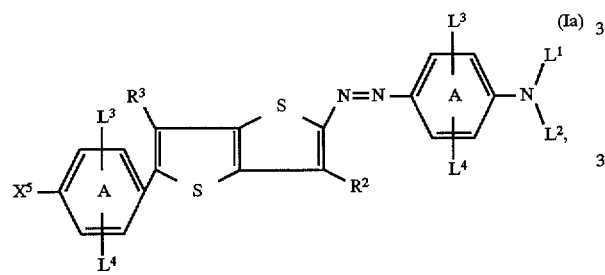

where
the ring A may be benzofused,
$L^1$ and $L^2$ are each independently of the other hydrogen, unsubstituted or phenyl-, hydroxyl-, acryloyloxy- or methacryloyloxy-substituted $C_1$-$C_{10}$-alkyl, or phenyl, or $L^1$ and $L^2$ are together with the nitrogen atom joining them together pyrrolidinyl, piperidinyl, morpholinyl, piperazinyl or N-($C_1$-$C_4$-alkyl)piperazinyl,
$L^3$ and $L^4$ are each independently of the other hydrogen, $C_1$-$C_{10}$-alkyl, $C_5$-$C_7$-cycloalkyl, $C_1$-$C_{10}$-alkoxy, cyano or halogen,
$X^5$ is hydrogen, nitro, hydroxysulfonyl, formyl, cyano, $C_1$-$C_4$-alkylsulfonyl, dicyanovinyl or a radical of the formula $COX^1$, $COOX^1$, $CONX^1X^2$, $CH=N-X^3$ or $CH=C(NO_2)-X^4$, wherein $X^1$ and $X^2$ are each independently of the other $C_1$-$C_{10}$-alkyl, which may be phenyl-substituted, $C_5$-$C_7$-cycloalkyl or phenyl, $X^3$ is hydroxyl or phenylamino and $X^4$ is hydrogen or $C_1$-$C_4$-alkyl,
$R^2$ is hydrogen, nitro, cyano, carboxyl or a radical of the formula $COX^1$, $COOX^1$ or $CONX^1X^2$, where $X^1$ and $X^2$ are each as defined above, and
$R^3$ is hydrogen, $C_1$-$C_{10}$-alkyl, which may be phenyl-substituted, $C_5$-$C_7$-cycloalkyl, phenyl or $C_1$-$C_{10}$-alkoxy.

Preference is given to azo dyes of the formula Ia where $L^1$ and $L^2$ are each independently of the other $C_1$-$C_4$-alkyl, $C_2$-$C_8$-hydroxyalkyl, $C_2$-$C_8$-acryloyloxyalkyl or $C_2$-$C_8$-methacryloyloxyalkyl, or $L^1$ and $L^2$ are together with the nitrogen atom joining them together pyrrolidinyl or piperidinyl.

Preference is further given to azo dyes of the formula Ia where $L^3$ and $L^4$ are each hydrogen.

Preference is further given to azo dyes of the formula Ia where the ring A is nonbenzofused.

Preference is further given to azo dyes of the formula Ia where $X^5$ is hydrogen, nitro, formyl, cyano, methylsulfonyl or dicyanovinyl, in particular cyano, $R^2$ is cyano and $R^3$ is hydrogen.

The azo dyes of the formula I can be prepared in a conventional manner, for example by diazotizing an amine of the formula II

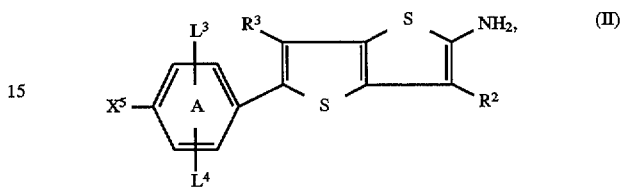

where the ring A, $L^3$, $L^4$, $X^5$, $R^2$ and $R^3$ are each as defined above, and coupling the resulting diazonium compound with a coupling component of the formula III

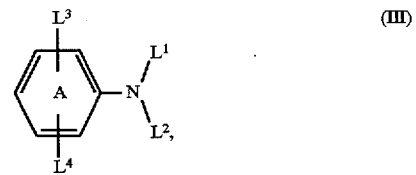

where the ring A, $L^1$, $L^2$, $L^3$ and $L^4$ are each as defined above.

The present invention further provides azo dye polymers containing as characteristic monomer units a bivalent radical derived from an azo dye of the formula I and also radicals of the formulae IV, V and VI

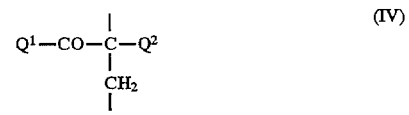

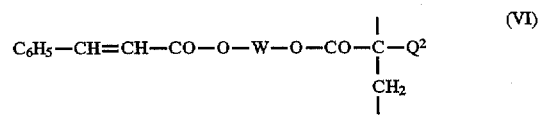

where
$Q^1$ is hydroxyl, $C_1$-$C_6$-alkoxy, oxiranylmethoxy, phenoxy, amino or mono- or di($C_1$-$C_4$-alkyl)amino,
$Q^2$ is hydrogen or methyl, and
W is $C_2$-$C_{10}$-alkylene,
wherein the proportion of the monomer units of the bivalent radicals derived from the formula I is from 1 to 100 mol %, that of those of the formula IV from 0 to 99 mol %, that of those of the formula V from 0 to 99 mol % and that of those of the formula VI from 0 to 75 mol %, in each case based on the polymer, the average molecular weight of the polymer being from 1000 to 500,000.

Preferably a bivalent radical derived from an azo dye of the formula I conforms to the formula VII

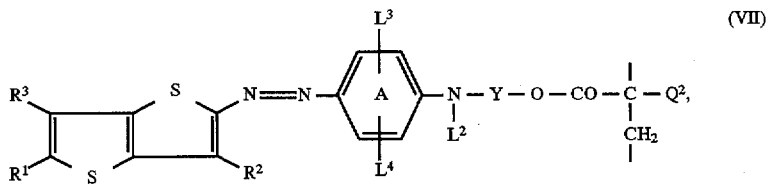

(VII)

where Y is $C_2$-$C_{10}$-alkylene and the ring A, $L^2$, $L^3$, $L^4$, $R^1$, $R^2$ and $Q^2$ are each as defined above.

The novel polymers can be prepared by methods known per se, as described for example in J. Polymer Sci., Part A, Polymer Chem. 28 (1990), 1–13.

Advantageously an appropriate azo dye of the formula I is reacted with an acryloyl compound of the formula VIII

where $Q^1$ and $Q^2$ are each as defined above, styrene and a cinnamic ester of the formula IX

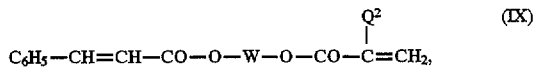

where $Q^2$ and W are each as defined above, in the above-mentioned molar ratio in an inert solvent (eg. toluene or xylene) in the presence of a free radical initiator (eg. azobisisobutyronitrile).

The polymers containing azo dyes of the formula I are advantageously suitable for use in nonlinear optics.

The compounds of the invention are thermally stable and have particularly large molecular hyperpolarizability values (β). In addition, the dyes are highly compatible with the polymers used in nonlinear optical systems and have good film-forming properties in copolymers.

The molecular hyperpolarizability can be determined for example by the method of solvatochromism (see for example Z. Naturforschung 20a (1965), 1441–1471, or J. Org. Chem. 54 (1989), 3775–3778). This method of measurement involves determining the position of the absorption band of a compound in different solvents, for example in dioxane or dimethyl sulfoxide. The shift of the absorption band is then directly proportional to the β value, ie. compounds having a large solvatochromic shift have a large molecular hyperpolarizability and are therefore highly suitable for use in nonlinear optical systems (see for example Chemistry and Industry, 1990, pages 600 to 608).

Of particular note is the suitability of the novel substances for use in communications technology, electrooptical modulators (eg. Mach-Zehnder interferometers), optical switches, frequency mixing or waveguides.

The Examples which follow illustrate the invention.

EXAMPLE 1

1.0 g (0.004 mol) of the compound of the formula

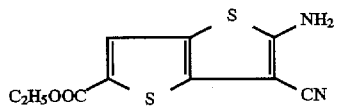

(prepared as described in Example 3 of U.S. Pat. No. 4,843,153) was suspended at 0°–5° C. in 20 ml of 17:3 v/v glacial acetic acid/propionic acid and admixed with 1.6 g of nitrosylsulfuric acid. After stirring at 5° C. for 1 h the resulting solution was added to a mixture of 0.65 g (0.004 mol) of N,N-diethylaniline in 5 ml of 17:3 v/v glacial acetic acid/propionic acid. The mixture was stirred for 30 min and then poured onto 250 ml of ice-water. The mixture was filtered with suction and the filter residue was washed with water. Drying under reduced pressure at 50° C. left 1.2 g of a red dye of the formula

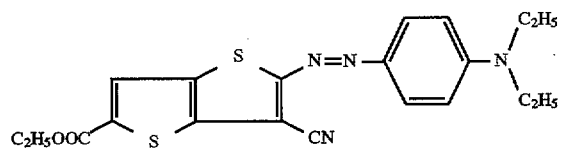

EXAMPLE 2

1.0 g (0.004 mol) of the compound of the formula

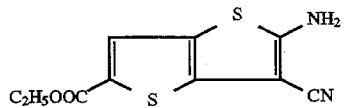

was suspended at 0°–5° C. in 20 ml of 17:3 v/v glacial acetic acid/propionic acid and admixed with 1.6 g of nitrosylsulfuric acid. After stirring at 5° C. for 1 h the resulting solution was added to a mixture of 0.65 g (0.004 mol) of N-phenylpyrrolidine and 5 ml of 17:3 v/v glacial acetic acid/propionic acid. The mixture was stirred for 30 min at 0° to 5° C. and then poured onto 250 ml of ice-water. The mixture was filtered with suction and the filter residue was washed with 1 l of water. Drying under reduced pressure at 50° C. left 1.13 g of a red dye of the formula

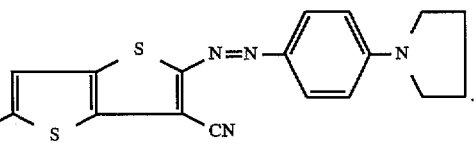

EXAMPLE 3

1.0 g (0.004 mol) of the compound of the formula

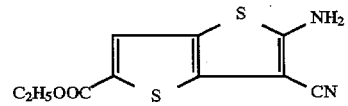

was suspended at 0°–5° C in 20 ml of 17:3 v/v glacial acetic acid/propionic acid and admixed with 1.16 g of nitrosylsulfuric acid. After stirring at 5° C. for 1 h the resulting solution was added to a mixture of 1.088 g (0.004 mol) of the compound of the formula

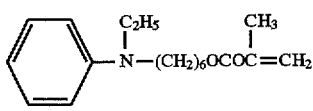

and 5 ml of 17:3 v/v glacial acetic acid/propionic acid. The mixture was stirred at 0°–5° C. for 30 min and then poured onto 250 ml of ice-water. The mixture was filtered off with suction and the filter residue was washed with 1 l of water. Drying under reduced pressure left 1.92 g of a dye of the formula

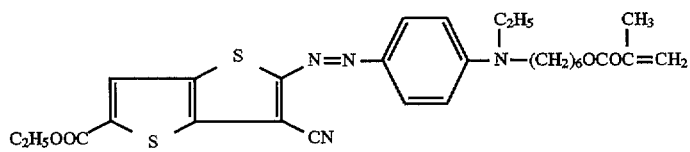

EXAMPLE 4 a) 73.15 g (0.21 mol) of the compound of the formula

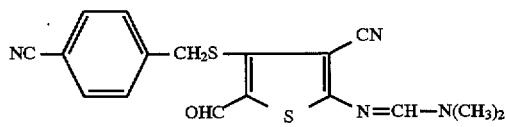

were heated in 370 ml of N,N-dimethylformamide at 100° C. for 7 h together with 25.5 g (0.33 mol) of sodium acetate. The resulting precipitate was then filtered off with suction, washed with water and dried at 50° C. under reduced pressure to yield 24.6 g of the compound of the formula

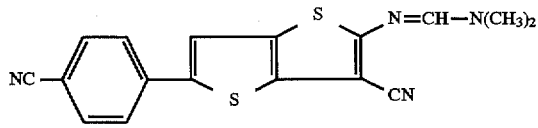

mp.: 243°–244° C. Analysis: calc C 67.08 H 3.97 N 18.41 S 10.53 found C 67.14 H 4.04 N 17.88 S 10.38 b) 7.8 g (0.023 mol) of the compound described in Example 4a were heated in 40 ml of N-methylpyrrolidone at 100° C. for 2 h in the presence of 4.6 g of concentrated hydrochloric acid. The reaction batch was then precipitated onto 500 g of ice-water, and the precipitate was filtered off with suction, washed with 200 ml of water and dried at 50° C. under reduced pressure to yield 6.6 g of a compound of the formula

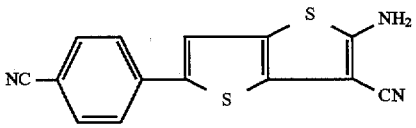

c) 4.78 g (0.017 mol) of the compound described in Example 4b were admixed at 0°–5° C. in 170 ml of 17:3 v/v glacial acetic acid/propionic acid with 5.34 g of nitrosylsulfuric acid. After subsequent stirring at 0°–5° C. for 2 h, 2.94 g (0.0187) of N-ethyl-N-(2-hydroxyethyl)aniline were added in the cold. After 2 h the precipitate was filtered off with suction, washed with water and dried under reduced pressure to yield 5.0 g of a dye of the formula

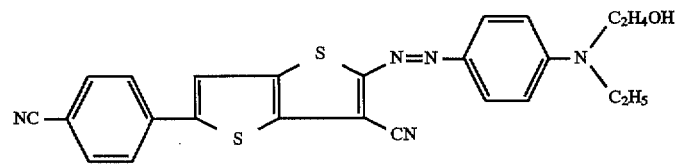

mp.: 272°–273° C. Analysis: calc C 63.00 H 4.19 O 3.5 N 15.31 S 14.01 found C 63.20 H 4.20 O 3.8 N 14.90 S 13.90

The same method produces the following compounds:

| Ex. No. | |
|---|---|
| 5 | 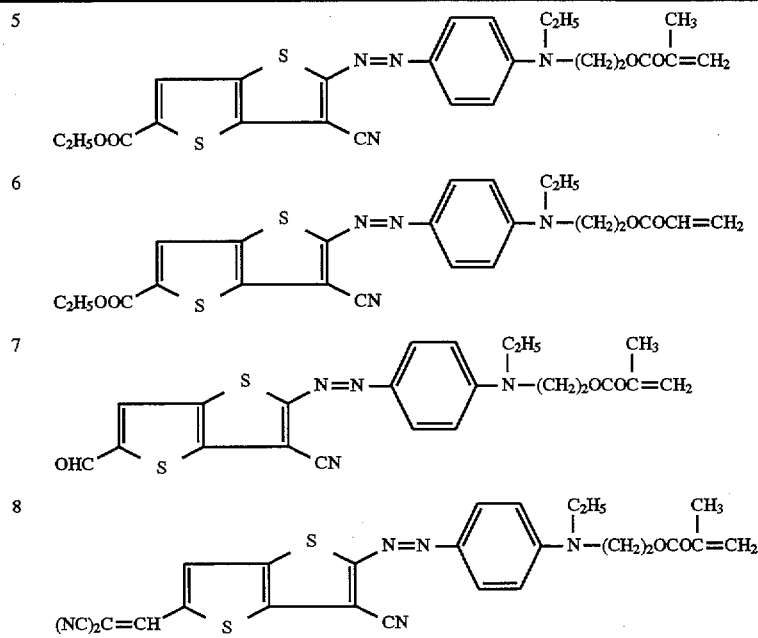 |
| 6 | |
| 7 | |
| 8 | |

The method described in Z. Naturforschung 20a (1965), 1441–1471, was employed to measure the absorption maximum of the individual dyes in both dioxane and dimethyl sulfoxide (DMSO) and then to determine the solvatochromic shift $\Delta \tilde{v}$ [cm$^{-1}$].

The respective results are listed in the following table:

TABLE

| Ex. No. | Dye No. | $\lambda_{max}$ (dioxane) [nm] | $\lambda_{max}$ (DMSO) [nm] | $\Delta \tilde{v}$ [cm$^{-1}$] |
|---|---|---|---|---|
| 9 | 1 | 550 | 583 | 1029 |
| 10 | 2 | 552 | 591 | 1195 |
| 11 | 3 | 558 | 590 | 972 |
| 12 | 4 | 568 | 595 | 799 |

We claim:

1. In a nonlinear optical system, the improvement comprising using an azo dye of the formula I

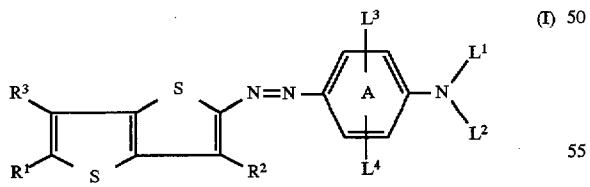 (I)

where
the ring A may be benzofused,

L$^1$ and L$^2$ are each independently of the other hydrogen, unsubstituted or phenyl-, hydroxyl-, acryloyloxy- or methacryloyloxy-substituted C$_1$-C$_{10}$-alkyl, or phenyl, or L$^1$ and L$^2$ are together with the nitrogen atom joining them together pyrrolidinyl, piperidinyl, morpholinyl, piperazinyl or N-(C$_1$-C$_4$-alkyl)piperazinyl, L$^3$ and L$^4$ are each independently of the other hydrogen, C$_1$-C$_{10}$-alkyl, C$_5$-C$_7$-cycloalkyl, C$_1$-C$_{10}$-alkoxy, cyano or halogen, R$^1$ is hydrogen, nitro, hydroxysulfonyl, carbamoyl, dicyanovinyl or a radical of the formula CONX$^1$X$^2$, CH=N—X$^3$, CH=C(NO$_2$)—X$^4$ or

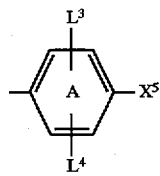

where X$^1$ and X$^2$ are each independently of the other C$_1$-C$_{10}$-alkyl, which may be phenyl-substituted, C$_5$-C$_7$-cycloalkyl or phenyl, X$^3$ is hydroxyl or phenylamino, X$^4$ is hydrogen or C$_1$-C$_4$-alkyl, and X$^5$ is hydrogen, nitro, hydroxysulfonyl, formyl, cyano, C$_1$-C$_4$-alkylsulfonyl, dicyanovinyl or a radical of the formula COX$^1$, COOX$^1$, CONX$^1$X$^2$, CH=N—X$^3$ or CH=C(NO$_2$)—X$^4$, where X$^1$, X$^2$, X$^3$ and X$^4$ are each as defined above, and the ring A and L$^3$ and L$^4$ are each as defined above, R$^2$ is hydrogen, nitro, cyano, carboxyl or a radical of the formula COX$^1$, COOX$^1$ OR CONX$^1$X$^2$, where X$^1$ and X$^2$ are each as defined above, and R$^3$ is hydrogen, C$_1$-C$_{10}$-alkyl, which may be phenyl-substituted, C$_5$-C$_7$-cycloalkyl, phenyl or C$_1$-C$_{10}$-alkoxy.

2. The nonlinear optical system as claimed in claim 1, wherefor L$^1$ and L$^2$ are each independently of the other C$_1$-C$_4$-alkyl, C$_2$-C$_8$-hydroxyalkyl, C$_2$-C$_8$-acryloyloxyalkyl or C$_2$-C$_8$-methacryloyloxyalkyl, or L$^1$ and L$^2$ are together with the nitrogen atom joining them together pyrrolidinyl or piperidinyl.

3. The nonlinear optical system as claimed in claim 1, wherefor L$^3$ and L$^4$ are each hydrogen.

4. The nonlinear optical system as claimed in claim 1, wherefor R$^1$ is dicyanovinyl or a radical of the formula

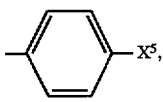

wherein $X^5$ is as defined in claim 1, $R^2$ is cyano and $R^3$ is hydrogen.

5. An azo dye of the formula Ia

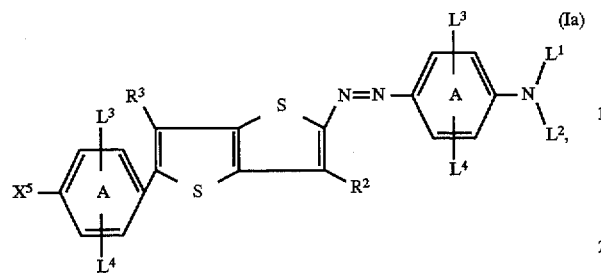

where
the ring A may be benzofused, $L^1$ and $L^2$ are each independently of the other hydrogen, unsubstituted or phenyl-, hydroxyl-, acryloyloxy- or methacryloyloxy-substituted $C_1$-$C_{10}$-alkyl, or phenyl, or $L^1$ and $L^2$ are together with the nitrogen atom joining them together pyrrolidinyl, piperidinyl, morpholinyl, piperazinyl or N-($C_1$-$C_4$-alkyl)piperazinyl, $L^3$ and $L^4$ are each independently of the other hydrogen, $C_1$-$C_{10}$-alkyl, $C_5$-$C_7$-cycloalkyl, $C_1$-$C_{10}$-alkoxy, cyano or halogen, $X^5$ is hydrogen, nitro, hydroxysulfonyl, formyl, cyano, $C_1$-$C_4$-alkylsulfonyl, dicyanovinyl or a radical of the formula $COX^1$, $COOX^1$, $CONX^1X^2$, CH=N—$X^3$ or CH=C(NO$_2$)—$X^4$, wherein $X^1$ and $X^2$ are each independently of the other $C_1$-$C_{10}$-alkyl, which may be phenyl-substituted, $C_5$-$C_7$-cycloalkyl or phenyl, $X^3$ is hydroxyl or phenylamino and $X^4$ is hydrogen or $C_1$-$C_4$-alkyl, $R^2$ is hydrogen, nitro, cyano, carboxyl or a radical of the formula $COX^1$, $COOX^1$ or $CONX^1X^2$, where $X^1$ and $X^2$ are each as defined above, and $R^3$ is hydrogen, $C_1$-$C_{10}$-alkyl, which may be phenyl-substituted, $C_5$-$C_7$-cycloalkyl, phenyl or $C_1$-$C_{10}$-alkoxy.

6. The azo dye as claimed in claim 5, wherein $L^1$ and $L^2$ are each independently of the other $C_1$-$C_4$-alkyl, $C_2$-$C_8$-hydroxyalkyl, $C_2$-$C_8$-acryloyloxyalkyl or $C_2$-$C_8$-methacryloyloxyalkyl, or $L^1$ and $L^2$ are together with the nitrogen atom joining them together pyrrolidinyl or piperidinyl.

7. The azo dye as claimed in claim 5, wherein $L^3$ and $L^4$ are each hydrogen.

8. The azo dye as claimed in claim 5, wherein $X^5$ is hydrogen, nitro, formyl, cyano, methylsulfonyl or dicyanovinyl, $R^2$ is cyano and $R^3$ is hydrogen.

9. In a nonlinear optical system, the improvement comprising using the azo dye polymer of claim 10.

10. An azo dye polymer containing as characteristic monomer units a bivalent radical derived from an azo dye of the formula I

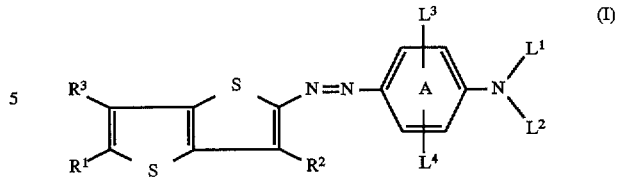

where
the ring A may be benzofused, $L^1$ and $L^2$ are each independently of the other hydrogen, unsubstituted or phenyl-, hydroxyl-, acryloyloxy- or methacryloyloxy-substituted $C_1$-$C_{10}$-alkyl, or phenyl, or $L^1$ and $L^2$ are together with the nitrogen atom joining them together pyrrolidinyl, piperidinyl, morpholinyl, piperazinyl or N-($C_1$-$C_4$-alkyl)piperazinyl, $L^3$ and $L^4$ are each independently of the other hydrogen, $C_1$-$C_{10}$-alkyl, $C_5$-$C_7$-cycloalkyl, $C_1$-$C_{10}$-alkoxy, cyano or halogen, $R^1$ is hydrogen, nitro, hydroxysulfonyl, carbamoyl, dicyanovinyl or a radical of the formula $CONX^1X^2$, CH=N—$X^3$, CH=C(NO$_2$)—$X^4$ or

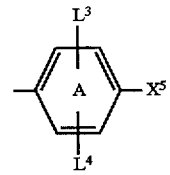

where $X^1$ and $X^2$ are each independently of the other $C_1$-$C_{10}$-alkyl, which may be phenyl-substituted, $C_5$-$C_7$-cycloalkyl or phenyl, $X^3$ is hydroxyl or phenylamino, $X^4$ is hydrogen or $C_1$-$C_4$-alkyl, and $X^5$ is hydrogen, nitro, hydroxysulfonyl, formyl, cyano, $C_1$-$C_4$-alkylsulfonyl, dicyanovinyl or a radical of the formula $COX^1$, $COOX^1$, $CONX^1X^2$, CH=N—$X^3$ or CH=C(NO$_2$)—$X^4$, where $X^1$, $X^2$, $X^3$ and $X^4$ are each as defined above, and the ring A and $L^3$ and $L^4$ are each as defined above, $R^2$ is hydrogen, nitro, cyano, carboxyl or a radical of the formula $COX^1$, $COOX^1$ OR $CONX^1X^2$, where $X^1$ and $X^2$ are each as defined above, and $R^3$ is hydrogen, $C_1$-$C_{10}$-alkyl, which may be phenyl-substituted, $C_5$-$C_7$-cycloalkyl, phenyl or $C_1$-$C_{10}$-alkoxy, and also radicals of the formulae IV, V and VI

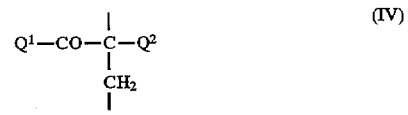

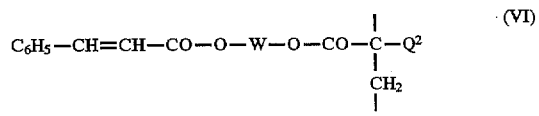

where
- $Q^1$ is hydroxyl, $C_1$-$C_6$-alkoxy, oxiranylmethoxy, phenoxy, amino or mono- or di($C_1$-$C_4$-alkyl)amino,
- $Q^2$ is hydrogen or methyl, and
- W is $C_2$-$C_{10}$-alkylene, wherein the proportion of the monomer units of the bivalent radicals derived from the formula I is from 1 to 100 mol %, that of those of the formula IV from 0 to 99 mol %, that of those of the formula V from 0 to 99 mol % and that of those of the formula VI from 0 to 75 mol %, in each case based on the polymer, the average molecular weight of the polymer being from 1000 to 500,000.

* * * * *